United States Patent
Poulin et al.

(10) Patent No.: US 11,926,664 B2
(45) Date of Patent: Mar. 12, 2024

(54) METHODS AND PHARMACEUTICAL COMPOSITIONS FOR MODULATING MONOCYTOPOIESIS

(71) Applicants: INSERM (INSTITUT NATIONAL DE LA SANTÉ ET DE LA RECHERCHE MÉDICALE), Paris (FR); INSTITUT PASTEUR DE LILLE, Lille (FR); CENTRE NATIONAL DE LA RECHERCHE SCIENTIFIQUE (CNRS), Paris (FR); UNIVERSITÉ DE LILLE, Lille (FR)

(72) Inventors: Lionel Poulin, Lille (FR); Corentin Lasseaux, Lille (FR); Mathias Chamaillard, Lille (FR)

(73) Assignees: INSERM (INSTITUT NATIONAL DE LA SANTÉ ET DE LA RECHERCHE MÉDICALE), Paris (FR); INSTITUT PASTEUR DE LILLE, Lille (FR); CENTRE NATIONAL DE LA RECHERCHE SCIENTIFIQUE (CNRS), Paris (FR); UNIVERSITÉ DE LILLE, Lille (FR)

( * ) Notice: Subject to any disclaimer, the term of this patent is extended or adjusted under 35 U.S.C. 154(b) by 903 days.

(21) Appl. No.: 16/633,900

(22) PCT Filed: Jul. 24, 2018

(86) PCT No.: PCT/EP2018/069973
§ 371 (c)(1),
(2) Date: Jan. 24, 2020

(87) PCT Pub. No.: WO2019/020593
PCT Pub. Date: Jan. 31, 2019

(65) Prior Publication Data
US 2020/0216530 A1 Jul. 9, 2020

(30) Foreign Application Priority Data

Jul. 25, 2017 (EP) .................................... 17305990

(51) Int. Cl.
*C07K 16/24* (2006.01)
*A61K 38/21* (2006.01)

(52) U.S. Cl.
CPC .......... *C07K 16/249* (2013.01); *A61K 38/212* (2013.01); *C07K 2317/76* (2013.01)

(58) Field of Classification Search
CPC ............. C07K 16/249; C07K 2317/76; A61K 38/212; A61K 2039/505; C12N 5/0639; C12N 2501/24; C12N 5/0645; Y02A 50/30
See application file for complete search history.

(56) References Cited

FOREIGN PATENT DOCUMENTS

WO 2008/068046 A1 6/2008
WO 2008/070135 A2 6/2008

OTHER PUBLICATIONS

Seo S. et al., Type I Interferon Signaling Regulates Ly6Chi Monocytes and Neutrophils during Acute Viral Pneumonia in Mice. PLOS Pathog 7(2): e1001304, Feb. 2011 (Year: 2011).*
Kumar V. et al., The Nature of Myeloid-Derived Suppressor Cells in the tumor Microenvironment, Trends Immunol, 37(3): 208-220, Mar. 2016 (Year: 2016).*
Snell L. et al., Type 1 Interferon in Chronic Virus Infection and Cancer, Trends Immunol, Aug. 2017, 38(8):542-557 (Available Online May 31, 2017) (Year: 2017).*
Hensel H. et al., Peripheral monocytosis as a predictive factor for adverse outcome in the emergency department, Medicine (Baltimore), 96:28(e7404), Jul. 14, 2017 (Year: 2017).*
Santangelo S. et al., Myeloid Commitment Shifts Toward Monocytopoiesis after Thermal Injury and Sepsis, Annals of Surgery, vol. 233, No. 1, 97-106, Jan. 2001 (Year: 2001).*
Tang Y. et al., Norepinephrine Modulates Myelopoiesis after Experimental Thermal Injury with Sepsis, Annals of Surgery, vol. 233, No. 2, 266-275, Feb. 2001 (Year: 2001).*
Dejager et al., Pharmacological Inhibition of Type I Interferon Signaling Protects Mice Against Lethal Sepsis, 2013, The Journal of Infectious Diseases, vol. 209, pp. 960-970 (Year: 2013).*
Danai et al., The Epidemiology of Sepsis in Patients With Malignancy, 2006, Chest Journal, vol. 129, Issue 6, pp. 1432-1440 (Year: 2006).*
Shindo et al., Anti-PD-L1 peptide improves survival in sepsis, 2017, Journal of Surgical Research, vol. 208, pp. 33-39 (Year: 2017).*
Guilliams et al., Unsupervised High-Dimensional Analysis Aligns Dendritic Cells across Tissues and Species, 2016, Immunity, vol. 45, pp. 669-684 (Year: 2016).*

(Continued)

*Primary Examiner* — Daniel E Kolker
*Assistant Examiner* — Brittney E Donoghue
(74) *Attorney, Agent, or Firm* — WC&F IP

(57) ABSTRACT

Monocytopoiesis is a hematological process that supplies the periphery with monocytes and subsequently with macrophages and monocyte-derived dendritic cells. Typically, monocytes circulate in the bloodstream for a very short time before undergoing apoptosis, however, stimulatory signals can trigger monocyte survival by inhibiting the apoptotic pathway, and thus contribute to the maintenance of the inflammatory response. Accordingly, there is a need for methods and pharmaceutical compositions for modulating monocytopoiesis. Now, the inventors show that type I interferons signaling promote the differentiation of monocyte-derived phagocytes at the level of their progenitors. Importantly, IFN-alpha and -beta were found to efficiently generate the development of monocyte-derived antigen-presenting cells while having no impact on the precursor activity of conventional dendritic cells. Accordingly, modulators of type I interferon (e.g. neutralizing antibodies or type I IFN polypeptides) would be suitable for modulating monocytopoiesis in subjects in need thereof.

7 Claims, No Drawings

(56) References Cited

OTHER PUBLICATIONS

Gautier et al., Enhanced Dendritic Cell Survival Attenuates Lipopolysaccharide-Induced Immunosuppression and Increases Resistance to Lethal Endotoxic Shock, The Journal of Immunology, 2008, vol. 10, pp. 6941-6946 (Year: 2008).*

Tagliaferri et al., New pharmacokinetic and pharmacodynamic tools for interferon-alpha (IFN-α) treatment of human cancer, 2005, Cancer Immunology, Immunotherapy, vol. 54, pp. 1-10 (Year: 2005).*

Kirkwood, Cancer Immunotherapy: The Interferon-α Experience, 2002, Seminars in Oncology, vol. 29, No. 3, pp. 18-26 (Year: 2002).*

Ferrantini et al., Interferon-α and cancer: Mechanisms of action and new perspectives of clinical use, 2007, Biochimie, vol. 89, pp. 884-893 (Year: 2007).*

Biotechne, IFN-alpha: Products, biotechne, R&D systems, retrieved from: https://www.rndsystems.com/target/ifn-alpha?category=Primary%20Antibodies&rnd_applications=Block/Neutralize (Year: 2023).*

Khamashta et al., Sifalimumab, an anti-interferon-α monoclonal antibody, in moderate to severe systemic lupus erythematosus: a randomised, double-blind, placebo-controlled study, 2016, Annals of the Rheumatic Disease, vol. 75, Issue 11, pp. 1909-1916 (Year: 2016).*

Duguet et al., S95021, a novel selective and pan-neutralizing anti interferon alpha (IFN-α) monoclonal antibody as a candidate treatment for selected autoimmune rheumatic diseases, 2021, Journal of Translational Autoimmunity, vol. 4, pp. 1-10 (Year: 2021).*

Buechler et al.; "Cutting Edge: Direct sensing of TLR7 Ligands and Type I IFN by the Common Myeloid Progenitor Promotes mTOR/P13K-Dependent Emergency Myelopoiesis"; The Journal of Immunology, vol. 197, No. 7, Aug. 26, 2016, pp. 2577-2582.

Müller et al.; "Type I Interferons and Natural Killer Cell Regulation in Cancer"; Frontiers in Immunology, vol. 8, Mar. 31, 2017, the whole document.

Parker et al.; "Antitumour actions of interferons: implication for cancer therapy"; Nature Reviews: Cancer, vol. 16, No. 3, Mar. 1, 2016, pp. 131-144.

Uematsu et al.; "Toll-like Receptors and Type I Interferons"; Journal of Biological Chemistry, vol. 282, No. 21, May 25, 2007, p. 15319-15323.

Buechler et al.; "Cutting Edge: Type I IFN Drives Emergency Myelopoisis and Peripheral Myeloid Expansion during Chronic TLR7 Signaling"; The Journal of Immunology, vol. 190, No. 3, Jan. 9, 2013, pp. 886-891.

Khamashta et al.; "Sifalimumab, an anti-inferon-[alpha] monoclonal antibody, in moderate to severe systemic lupus erythematosus: a randomised, double-blind, placebo-controlled study"; Annals of the Rheumatic Diseases, vol. 75, No. 11, Mar. 23, 2016, pp. 1909-1916.

Di Franco et al.; "Role of Type I and II Interferons in Colorectal Cancer and Melanoma"; Frontiers in Immunology, vol. 8, Jul. 26, 2017, the whole document.

Lasseaux et al.; "Type I interferons drive inflammasome-independent emergency monocytopoiesis during endotoxemia"; Scientific Reports, vol. 7, No. 1, Dec. 1, 2017, abstract, pp. 2, 6-10.

* cited by examiner

METHODS AND PHARMACEUTICAL COMPOSITIONS FOR MODULATING MONOCYTOPOIESIS

FIELD OF THE INVENTION

The present invention relates to methods and pharmaceutical compositions for modulating monocytopoiesis.

BACKGROUND OF THE INVENTION

Monocytopoiesis is a hematological process that supplies the periphery with monocytes and subsequently with macrophages and monocyte-derived dendritic cells. Monocytes play central roles in the initiation and resolution of inflammation, principally through phagocytosis, the release of inflammatory cytokines, reactive oxygen species and the activation of the acquired immune system. Typically, monocytes circulate in the bloodstream for a very short time before undergoing apoptosis, however, stimulatory signals can trigger monocyte survival by inhibiting the apoptotic pathway, and thus contribute to the maintenance of the inflammatory response. During the inflammatory response, monocytes are recruited to the sites of inflammation. This recruitment is essential for effective control and clearance of infection, but recruited monocytes also contribute to the pathogenesis of inflammatory and degenerative diseases. The accumulation of monocytes can be harmful and aggravate disease such as atherosclerosis, arthritis, and multiple sclerosis. Resolution of inflammation requires the reduction and/or inhibition of inflammatory cells to the inflammatory foci, and apoptosis of the inflammatory cells already present.

In particular, emergency monocytopoiesis is thought to modulate hematopoietic stem and progenitor cells (HSPCs) and non-self-renewing precursors that express TLR4[1]. Indeed, it has been suggested that TLR activation alters the function and fate of HSPCs[2]. There are several DC subsets, which originate from either monocytic precursors differentiating into monocyte-derived antigen-presenting cells (Mo-APCs) or from non-monocytic progenitors differentiating into conventional DCs (cDCs)[3,4]. The latter can be further divided into two subsets (namely cDC1 and cDC2[3]), both of which can be generated by in vitro culture of bone marrow cells with the cDC growth factor FMS-related tyrosine kinase 3 ligand (Flt3-L)[5]. DCs are generally studied by characterizing their surface markers; all the subsets display the integrin CD11c and major histocompatibility complex class II (MHCII). We and others have shown that the surface markers CD64 (also known as FcγRI) and MerTK are specific for Mo-APCs, allowing the distinction between such cells and cDC[3,6-9]. DCs are part of the mononuclear phagocyte lineage, which originate from the bipotent macrophage and DC progenitor (MDP). The latter can differentiate into either a common monocyte progenitor (cMoP)[10] or a cDC precursor (CDP)[11]. The CDPs give rise to pre-DCs, which migrate from the bone marrow to produce cDCs in peripheral tissues[11]. Due to the DCs' protective role during sepsis, some researchers have argued that maintaining DC function should be a key objective in this field[12-16]. However, most of the studies in this area were performed before it became possible to distinguish between cDCs and monocyte-derived APCs with the marker CD64[3,4]. In this context, several inflammatory cytokines (such as IFNα) favor the proliferation of hematopoietic stem cells with a bias towards the myelomonocytic hematopoietic branch, although IFNα has also been described as an inhibitor of hematopoiesis[17].

Sepsis is a relatively common, life-threatening syndrome in which a systemic bacterial infection triggers a dysregulated host inflammatory response and leading to an immunosuppressive state associated with the development of secondary and nosocomial infections[18-20]. Although the inflammatory response is often brought under control in the intensive care unit, the immunosuppressive state appears to increase subsequently the likelihood of death in sepsis patients[18,21]. Although specific antisepsis treatments and reliable sepsis biomarkers are still lacking[22], dendritic cells (DCs) are considered to be crucial for the resolution of sepsis and to combat life-threatening infection[16,23-30]. Notably, *Escherichia coli* is a major cause of sepsis in hospitalized patients[31]. The cell wall of *E. coli* contains lipopolysaccharide (LPS), which triggers the expression of type I interferon (IFN)[32], upon its recognition by Toll-like receptor 4 (TLR4). Type I IFNs constitute a multigene family whose main members (IFNα and IFNβ) have a major role in mediating the lethal effects of septic shock[33-35]. Type I IFNs exert their biological effects by binding to at least two transmembrane receptors (Ifnar1 and Ifnar2) and thus activating intracellular pathways leading to the expression of various IFN regulated genes[36,37]. On one hand, type I IFNs are required for the successful resolution of infections. On the other, type I IFNs are harmful when their overproduction leads to septic shock[19]. This duality may explain why in vivo experiments in mouse models have prompted different conclusions about their involvement in sepsis[38]. Consequently, the type I IFNs' exact role in sepsis has yet to be clearly defined.

SUMMARY OF THE INVENTION

The present invention relates to methods and pharmaceutical compositions for modulating monocytopoiesis. In particular, the present invention is defined by the claims.

DETAILED DESCRIPTION OF THE INVENTION

The inventors show that type I interferons signaling promote the differentiation of monocyte-derived phagocytes at the level of their progenitors during a mouse model of endotoxemia. In this model, they characterized early changes in the numbers of conventional dendritic cells, monocyte-derived antigen-presenting cells (Mo-APC) and their respective precursors. While loss of caspase-1 failed to impair a shift toward monocytopoiesis, the inventors observed sustained type-I-IFN-dependent monocyte progenitors differentiation in the bone marrow correlated to an accumulation of Mo-APCs in the spleen. Importantly, IFN-alpha and -beta were found to efficiently generate the development of monocyte-derived antigen-presenting cells while having no impact on the precursor activity of conventional dendritic cells. Consistently, the depletion of conventional dendritic cells and their direct precursor occurred independently of type-I-IFN signaling in vivo. This characterization of early changes in mononuclear phagocytes and their dependency on type I IFN signaling opens the way to the development of treatments for modulating monocytopoiesis.

Accordingly, the first object of the present invention relates to a method of reducing monocytopoiesis in a patient in need thereof comprising administering to the patient a therapeutically effective amount of inhibitor of type I interferons.

The method of the present invention are thus particularly suitable for the treatment of monocyte-dependent inflammatory disorders. More particularly, the methods of the present invention are particular suitable for reducing inflammatory monocyte accumulation at the primary site of inflammation. Examples of monocyte-dependent inflammatory disorders include but are not limited to arthritis, rheumatoid arthritis, acute arthritis, chronic rheumatoid arthritis, gouty arthritis, acute gouty arthritis, chronic inflammatory arthritis, degenerative arthritis, infectious arthritis, Lyme arthritis, proliferative arthritis, psoriatic arthritis, vertebral arthritis, and juvenile-onset rheumatoid arthritis, osteoarthritis, arthritis chronica progrediente, arthritis deformans, polyarthritis chronica primaria, reactive arthritis, and ankylosing spondylitis), inflammatory hyperproliferative skin diseases, psoriasis such as plaque psoriasis, gutatte psoriasis, pustular psoriasis, and psoriasis of the nails, dermatitis including contact dermatitis, chronic contact dermatitis, allergic dermatitis, allergic contact dermatitis, dermatitis herpetiformis, and atopic dermatitis, x-linked hyper IgM syndrome, urticaria such as chronic allergic urticaria and chronic idiopathic urticaria, including chronic autoimmune urticaria, polymyositis/dermatomyositis, juvenile dermatomyositis, toxic epidermal necrolysis, scleroderma, systemic scleroderma, sclerosis, systemic sclerosis, multiple sclerosis (MS), spino-optical MS, primary progressive MS (PPMS), relapsing remitting MS (RRMS), progressive systemic sclerosis, atherosclerosis, arteriosclerosis, sclerosis disseminata, and ataxic sclerosis, inflammatory bowel disease (IBD), Crohn's disease, colitis, ulcerative colitis, colitis ulcerosa, microscopic colitis, collagenous colitis, colitis polyposa, necrotizing enterocolitis, transmural colitis, autoimmune inflammatory bowel disease, pyoderma gangrenosum, erythema nodosum, primary sclerosing cholangitis, episcleritis, respiratory distress syndrome, adult or acute respiratory distress syndrome (ARDS), meningitis, inflammation of all or part of the uvea, iritis, choroiditis, an autoimmune hematological disorder, rheumatoid spondylitis, sudden hearing loss, IgE-mediated diseases such as anaphylaxis and allergic and atopic rhinitis, encephalitis, Rasmussen's encephalitis, limbic and/or brainstem encephalitis, uveitis, anterior uveitis, acute anterior uveitis, granulomatous uveitis, non-granulomatous uveitis, phacoantigenic uveitis, posterior uveitis, autoimmune uveitis, glomerulonephritis (GN), idiopathic membranous GN or idiopathic membranous nephropathy, membrano- or membranous proliferative GN (MPGN), rapidly progressive GN, allergic conditions, autoimmune myocarditis, leukocyte adhesion deficiency, systemic lupus erythematosus (SLE) or systemic lupus erythematodes such as cutaneous SLE, subacute cutaneous lupus erythematosus, neonatal lupus syndrome (NLE), lupus erythematosus disseminatus, lupus (including nephritis, cerebritis, pediatric, non-renal, extra-renal, discoid, alopecia), juvenile onset (Type I) diabetes mellitus, including pediatric insulin-dependent diabetes mellitus (IDDM), adult onset diabetes mellitus (Type II diabetes), autoimmune diabetes, idiopathic diabetes insipidus, immune responses associated with acute and delayed hypersensitivity mediated by cytokines and T-lymphocytes, tuberculosis, sarcoidosis, granulomatosis, lymphomatoid granulomatosis, Wegener's granulomatosis, agranulocytosis, vasculitides, including vasculitis, large vessel vasculitis, polymyalgia rheumatica, giant cell (Takayasu's) arteritis, medium vessel vasculitis, Kawasaki's disease, polyarteritis nodosa, microscopic polyarteritis, CNS vasculitis, necrotizing, cutaneous, hypersensitivity vasculitis, systemic necrotizing vasculitis, and ANCA-associated vasculitis, such as Churg-Strauss vasculitis or syndrome (CSS), temporal arteritis, aplastic anemia, autoimmune aplastic anemia, Coombs positive anemia, Diamond Blackfan anemia, hemolytic anemia or immune hemolytic anemia including autoimmune hemolytic anemia (AIHA), pernicious anemia (anemia perniciosa), Addison's disease, pure red cell anemia or aplasia (PRCA), Factor VIII deficiency, hemophilia A, autoimmune neutropenia, pancytopenia, leukopenia, diseases involving leukocyte diapedesis, CNS inflammatory disorders, multiple organ injury syndrome such as those secondary to septicemia, trauma or hemorrhage, antigen-antibody complex-mediated diseases, anti-glomerular basement membrane disease, anti-phospholipid antibody syndrome, allergic neuritis, Bechet's or Behcet's disease, Castleman's syndrome, Goodpasture's syndrome, Reynaud's syndrome, Sjogren's syndrome, Stevens-Johnson syndrome, pemphigoid such as pemphigoid bullous and skin pemphigoid, pemphigus, optionally pemphigus vulgaris, pemphigus foliaceus, pemphigus mucus-membrane pemphigoid, pemphigus erythematosus, autoimmune polyendocrinopathies, Reiter's disease or syndrome, immune complex nephritis, antibody-mediated nephritis, neuromyelitis optica, polyneuropathies, chronic neuropathy, IgM polyneuropathies, IgM-mediated neuropathy, thrombocytopenia, thrombotic thrombocytopenic purpura (TTP), idiopathic thrombocytopenic purpura (ITP), autoimmune orchitis and oophoritis, primary hypothyroidism, hypoparathyroidism, autoimmune thyroiditis, Hashimoto's disease, chronic thyroiditis (Hashimoto's thyroiditis); subacute thyroiditis, autoimmune thyroid disease, idiopathic hypothyroidism, Grave's disease, polyglandular syndromes such as autoimmune polyglandular syndromes (or polyglandular endocrinopathy syndromes), paraneoplastic syndromes, including neurologic paraneoplastic syndromes such as Lambert-Eaton myasthenic syndrome or Eaton-Lambert syndrome, stiff-man or stiff-person syndrome, encephalomyelitis, allergic encephalomyelitis, experimental allergic encephalomyelitis (EAE), myasthenia gravis, thymoma-associated myasthenia gravis, cerebellar degeneration, neuromyotonia, opsoclonus or opsoclonus myoclonus syndrome (OMS), and sensory neuropathy, multifocal motor neuropathy, Sheehan's syndrome, autoimmune hepatitis, chronic hepatitis, lupoid hepatitis, giant cell hepatitis, chronic active hepatitis or autoimmune chronic active hepatitis, lymphoid interstitial pneumonitis, bronchiolitis obliterans (non-transplant) vs NSIP, Guillain-Barre syndrome, Berger's disease (IgA nephropathy), idiopathic IgA nephropathy, linear IgA dermatosis, primary biliary cirrhosis, pneumonocirrhosis, autoimmune enteropathy syndrome, Celiac disease, Coeliac disease, celiac sprue (gluten enteropathy), refractory sprue, idiopathic sprue, cryoglobulinemia, amylotrophic lateral sclerosis (ALS; Lou Gehrig's disease), coronary artery disease, autoimmune ear disease such as autoimmune inner ear disease (AGED), autoimmune hearing loss, opsoclonus myoclonus syndrome (OMS), polychondritis such as refractory or relapsed polychondritis, pulmonary alveolar proteinosis, amyloidosis, scleritis, a non-cancerous lymphocytosis, a primary lymphocytosis, which includes monoclonal B cell lymphocytosis, optionally benign monoclonal gammopathy or monoclonal garnmopathy of undetermined significance, MGUS, peripheral neuropathy, paraneoplastic syndrome, channelopathies such as epilepsy, migraine, arrhythmia, muscular disorders, deafness, blindness, periodic paralysis, and channelopathies of the CNS, autism, inflammatory myopathy, focal segmental glomerulosclerosis (FSGS), endocrine opthalmopathy, uveoretinitis, chlorioretinitis, autoimmune hepatological disorder, fibromyalgia, multiple endocrine failure, Schmidt's syndrome, adrenalitis, gastric atrophy, presenile dementia, demyelinating diseases such as autoimmune demyelinating diseases, diabetic nephropathy, Dressler's syndrome, alopecia greata, CREST syndrome (calcinosis, Raynaud's phenomenon, esophageal dysmotility, sclerodactyl), and telangiectasia), male and female autoimmune infertility, mixed connective tissue disease, Chagas' disease, rheumatic fever, recurrent abortion, farmer's lung, erythema multiforme, post-cardiotomy syndrome, Cushing's syndrome, bird-fancier's lung, allergic granulomatous angiitis, benign lymphocytic angiitis, Alport's syndrome, alveolitis such as allergic alveolitis and fibrosing alveolitis, interstitial lung disease, transfusion reaction, leprosy, malaria, leishmaniasis, kypanosomiasis, schistosomiasis, ascariasis, aspergillosis, Sampter's syndrome, Caplan's syndrome, dengue, endocarditis, endomyocardial fibrosis, diffuse interstitial pulmonary fibrosis, interstitial lung fibrosis, idiopathic pulmonary fibrosis, cystic fibrosis, endophthalmitis, erythema elevatum et diutinum, erythroblastosis fetalis, eosinophilic faciitis, Shulman's syndrome, Felty's syndrome, flariasis, cyclitis such as chronic cyclitis, heterochronic cyclitis, iridocyclitis, or Fuch's cyclitis, Henoch-Schonlein purpura, human immunodeficiency virus (HIV) infection, echovirus infection, cardiomyopathy, Alzheimer's disease, parvovirus infection, rubella virus infection, post-vaccination syndromes, congenital rubella infection, Epstein-Barr virus infection, mumps, Evan's syndrome, autoimmune gonadal failure, Sydenham's chorea, post-streptococcal nephritis, thromboangitis ubiterans, thyrotoxicosis, tabes dorsalis, chorioiditis, giant cell polymyalgia, endocrine ophthamopathy, chronic hypersensitivity pneumonitis, keratoconjunctivitis sicca, epidemic keratoconjunctivitis, idiopathic nephritic syndrome, minimal change nephropathy, benign familial and ischemia-reperfusion injury, retinal autoimmunity, joint inflammation, bronchitis, chronic obstructive airway disease, silicosis, aphthae, aphthous stomatitis, arteriosclerotic disorders, aspermiogenese, autoimmune hemolysis, Boeck's disease, cryoglobulinemia, Dupuytren's contracture, endophthalmia phacoanaphylactica, enteritis allergica, erythema nodosum leprosum, idiopathic facial paralysis, chronic fatigue syndrome, febris rheumatica, Hamman-Rich's disease, sensoneural hearing loss, haemoglobinuria paroxysmatica, hypogonadism, ileitis regionalis, leucopenia, mononucleosis infectiosa, traverse myelitis, primary idiopathic myxedema, nephrosis, ophthalmia symphatica, orchitis granulomatosa, pancreatitis (e.g. chronic pancreatitis), polyradiculitis acuta, pyoderma gangrenosum, Quervain's thyreoiditis, acquired splenic atrophy, infertility due to antispermatozoan antibodies, non-malignant thymoma, vitiligo, SCID and Epstein-Barr virus-associated diseases, acquired immune deficiency syndrome (AIDS), parasitic diseases such as Lesihmania, toxic-shock syndrome, food poisoning, conditions involving infiltration of T cells, leukocyte-adhesion deficiency, immune responses associated with acute and delayed hypersensitivity mediated by cytokines and T-lymphocytes, diseases involving leukocyte diapedesis, multiple organ injury syndrome, antigen-antibody complex-mediated diseases, antiglomerular basement membrane disease, allergic neuritis, autoimmune polyendocrinopathies, oophoritis, primary myxedema, autoimmune atrophic gastritis, sympathetic ophthalmia, rheumatic diseases, mixed connective tissue disease, nephrotic syndrome, insulitis, polyendocrine failure, peripheral neuropathy, autoimmune polyglandular syndrome type I, adult-onset idiopathic hypoparathyroidism (AOIH), alopecia totalis, dilated cardiomyopathy, epidermolisis bullosa acquisita (EBA), hemochromatosis, myocarditis, nephrotic syndrome, primary sclerosing cholangitis, purulent or nonpurulent sinusitis, acute or chronic sinusitis, ethmoid, frontal, maxillary, or sphenoid sinusitis, an eosinophil-related disorder such as eosinophilia, pulmonary infiltration eosinophilia, eosinophilia-myalgia syndrome, Loffler's syndrome, chronic eosinophilic pneumonia, tropical pulmonary eosinophilia, bronchopneumonic aspergillosis, aspergilloma, or granulomas containing eosinophils, anaphylaxis, seronegative spondyloarthritides, polyendocrine autoimmune disease, sclerosing cholangitis, sclera, episclera, chronic mucocutaneous candidiasis, Bruton's syndrome, transient hypogammaglobulinemia of infancy, Wiskott-Aldrich syndrome, ataxia telangiectasia, autoimmune disorders associated with collagen disease, rheumatism, neurological disease, ischemic re-perfusion disorder, reduction in blood pressure response, vascular dysfunction, antgiectasis, tissue injury, cardiovascular ischemia, hyperalgesia, cerebral ischemia, and disease accompanying vascularization, allergic hypersensitivity disorders, glomerulonephritides, reperfusion injury, reperfusion injury of myocardial or other tissues, dermatoses with acute inflammatory components, acute purulent meningitis or other central nervous system inflammatory disorders, ocular and orbital inflammatory disorders, granulocyte transfusion-associated syndromes, cytokine-induced toxicity, acute serious inflammation, chronic intractable inflammation, pyelitis, pneumonocirrhosis, diabetic retinopathy, diabetic large-artery disorder, endarterial hyperplasia, peptic ulcer, valvulitis, and endometriosis.

In some embodiments, the method of the present invention would be suitable for the treatment of early acute sepsis phase. As used herein, the term "systemic inflammatory response syndrome" (or "SIRS") is in accordance with its normal meaning, to refer to an inflammatory state of the whole body without a source of infection. There are four major diagnostic symptoms of SIRS, although any two of these are enough for a diagnosis (see e.g. Nystrom (1998) Journal of Antimicrobial Chemotherapy, 41, Suppl A, 1-7). As used herein, the term "sepsis" refers to a form of SIRS which is caused by a suspected or proven infection (see e.g. Nystrom (1998) Journal of Antimicrobial Chemotherapy, 41, Suppl. A, 1-7). An infection that leads to sepsis may be caused by e.g. a virus, a fungus, a protozoan or a bacterium.

In some embodiments, the method of the present invention are particularly suitable for the treatment of cancer by inhibiting the tumor infiltration of monocytic myeloid-derived suppressor cells which possess strong immunosuppressive activities. As used herein, the term "cancer" has its general meaning in the art and includes, but is not limited to, solid tumors and blood borne tumors. The term cancer includes diseases of the skin, tissues, organs, bone, cartilage, blood and vessels. The term "cancer" further encompasses both primary and metastatic cancers. Examples of cancers that may be treated by methods and compositions of the present invention include, but are not limited to, cancer cells from the bladder, blood, bone, bone marrow, brain, breast, colon, esophagus, gastrointestine, gum, head, kidney, liver, lung, nasopharynx, neck, ovary, prostate, skin, stomach, testis, tongue, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous; adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; and roblastoma, malignant; Sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; Hodgkin's lymphoma; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

In some embodiments, the methods of the present invention comprise administering the patient suffering from cancer with a therapeutically effective combination of an inhibitor of type I interferons with an immune checkpoint inhibitor.

As used herein, the term "immune checkpoint inhibitor" has its general meaning in the art and refers to any compound inhibiting the function of an immune inhibitory checkpoint protein. As used herein the term "immune checkpoint protein" has its general meaning in the art and refers to a molecule that is expressed by T cells in that either turn up a signal (stimulatory checkpoint molecules) or turn down a signal (inhibitory checkpoint molecules). Immune checkpoint molecules are recognized in the art to constitute immune checkpoint pathways similar to the CTLA-4 and PD-1 dependent pathways (see e.g. Pardoll, 2012. Nature Rev Cancer 12:252-264; Mellman et al., 2011. Nature 480:480-489). Examples of inhibitory checkpoint molecules include A2AR, B7-H3, B7-H4, BTLA, CTLA-4, CD277, IDO, KIR, PD-1, LAG-3, TIM-3 and VISTA. Inhibition includes reduction of function and full blockade. Preferred immune checkpoint inhibitors are antibodies that specifically recognize immune checkpoint proteins. A number of immune checkpoint inhibitors are known and in analogy of these known immune checkpoint protein inhibitors, alternative immune checkpoint inhibitors may be developed in the (near) future. The immune checkpoint inhibitors include peptides, antibodies, nucleic acid molecules and small molecules.

In some embodiments, the immune checkpoint inhibitor is an antibody selected from the group consisting of anti-CTLA4 antibodies, anti-PD-1 antibodies, anti-PD-L1 antibodies, anti-PD-L2 antibodies anti-TIM-3 antibodies, anti-LAG3 antibodies, anti-B7H3 antibodies, anti-B7H4 antibodies, anti-BTLA antibodies, and anti-B7H6 antibodies.

Examples of anti-CTLA-4 antibodies are described in U.S. Pat. Nos. 5,811,097; 5,811,097; 5,855,887; 6,051,227; 6,207,157; 6,682,736; 6,984,720; and 7,605,238. One anti-CTLA-4 antibody is tremelimumab, (ticilimumab, CP-675, 206). In some embodiments, the anti-CTLA-4 antibody is ipilimumab (also known as 10D1, MDX-D010) a fully human monoclonal IgG antibody that binds to CTLA-4.

Other immune-checkpoint inhibitors include lymphocyte activation gene-3 (LAG-3) inhibitors, such as IMP321, a soluble Ig fusion protein (Brignone et al., 2007, J. Immunol. 179:4202-4211). Other immune-checkpoint inhibitors include B7 inhibitors, such as B7-H3 and B7-H4 inhibitors. In particular, the anti-B7-H3 antibody MGA271 (Loo et al., 2012, Clin. Cancer Res. July 15 (18) 3834). Also included are TIM3 (T-cell immunoglobulin domain and mucin domain 3) inhibitors (Fourcade et al., 2010, J. Exp. Med. 207:2175-86 and Sakuishi et al., 2010, J. Exp. Med. 207: 2187-94). As used herein, the term "TIM-3" has its general meaning in the art and refers to T cell immunoglobulin and mucin domain-containing molecule 3. The natural ligand of TIM-3 is galectin 9 (Gal9). Accordingly, the term "TIM-3 inhibitor" as used herein refers to a compound, substance or composition that can inhibit the function of TIM-3. For example, the inhibitor can inhibit the expression or activity of TIM-3, modulate or block the TIM-3 signaling pathway and/or block the binding of TIM-3 to galectin-9. Antibodies having specificity for TIM-3 are well known in the art and typically those described in WO2011155607, WO2013006490 and WO2010117057.

In some embodiments, the immune checkpoint inhibitor is an IDO inhibitor. Examples of IDO inhibitors are described in WO 2014150677. Examples of IDO inhibitors include without limitation 1-methyl-tryptophan (IMT), β-(3-benzofuranyl)-alanine, β-(3-benzo(b)thienyl)-alanine), 6-nitro-tryptophan, 6-fluoro-tryptophan, 4-methyl-tryptophan, 5-methyl tryptophan, 6-methyl-tryptophan, 5-methoxy-tryptophan, 5-hydroxy-tryptophan, indole 3-carbinol, 3,3'-diindolylmethane, epigallocatechin gallate, 5-Br-4-Cl-indoxyl 1,3-diacetate, 9-vinylcarbazole, acemetacin, 5-bromo-tryptophan, 5-bromoindoxyl diacetate, 3-Amino-naphtoic acid, pyrrolidine dithiocarbamate, 4-phenylimidazole a brassinin derivative, a thiohydantoin derivative, a β-carboline derivative or a brassilexin derivative. Preferably the IDO inhibitor is selected from 1-methyl-tryptophan, β-(3-benzofuranyl)-alanine, 6-nitro-L-tryptophan, 3-Amino-naphtoic acid and β-[3-benzo(b)thienyl]-alanine or a derivative or prodrug thereof.

In some embodiments, the immune checkpoint inhibitor is a PD-1 inhibitor.

Accordingly, the term "PD-1 inhibitor" as used herein refers to a compound, substance or composition that can inhibit the function of PD-1. For example, the inhibitor can inhibit the expression or activity of PD-1, modulate or block the PD-1 signaling pathway and/or block the binding of PD-1 to PD-L1 or PD-L2. In some embodiments, the PD-1 inhibitor is an antibody directed against the extracellular domain of PD-1. In some embodiments, the PD-1 inhibitor is an antibody directed against the extracellular domain of PD-L1. Examples of PD-1 and PD-L1 antibodies are described in U.S. Pat. Nos. 7,488,802; 7,943,743; 8,008,449; 8,168,757; 8,217,149, and PCT Published Patent Application Nos.: WO03042402, WO2008156712, WO2010089411, WO2010036959, WO2011066342, WO2011159877, WO2011082400, and WO2011161699. In some embodiments, the PD-1 blockers include anti-PD-L1 antibodies. In certain other embodiments the PD-1 blockers include anti-PD-1 antibodies and similar binding proteins such as nivolumab (MDX 1106, BMS 936558, ONO 4538), a fully human IgG4 antibody that binds to and blocks the activation of PD-1 by its ligands PD-L1 and PD-L2; lambrolizumab (MK-3475 or SCH 900475), a humanized monoclonal IgG4 antibody against PD-1; CT-011 a humanized antibody that binds PD-1; AMP-224 is a fusion protein of B7-DC; an antibody Fc portion; BMS-936559 (MDX-1105-01) for PD-L1 (B7-H1) blockade. In some embodiments, the PD-1 inhibitor is a small molecule or peptide, or a peptide derivative, such as those described in U.S. Pat. Nos. 8,907,053; 9,096,642; and 9,044,442 and U S Patent Application Publication No 2015/0087581; 1,2,4 oxadiazole compounds and derivatives such as those described in U.S. Patent Application Publication No. 2015/0073024; cyclic peptidomimetic compounds and derivatives such as those described in U.S. Patent Application Publication No. 2015/0073042; cyclic compounds and derivatives such as those described in U.S. Patent Application Publication No. 2015/0125491; 1,3,4 oxadiazole and 1,3,4 thiadiazole compounds and derivatives such as those described in International Patent Application Publication No. WO 2015/033301; peptide-based compounds and derivatives such as those described in International Patent Application Publication Nos. WO 2015/036927 and WO 2015/04490, or a macrocyclic peptide-based compounds and derivatives such as those described in U.S. Patent Application Publication No. 2014/0294898; the disclosures of each of which are hereby incorporated by reference in their entireties.

As used herein, the term "type I interferon" has its general meaning in the art and refers to members of the type I interferon family of molecules that are ligands for IFNAR-1 (i.e., members of the type I interferon family of molecules that are capable of binding IFNAR-1). Examples of type I interferon ligands are interferon alpha 1, 2a, 2b, 4, 5, 6, 7, 8, 10, 14, 16, 17, 21, interferon beta and interferon omega. The term "interferon-α" (IFNα) as used herein refers to all native subtypes of human alpha interferons. Native IFNα consists of more than 23 closely related protein subtypes encoded by distinct genes with a high degree of structural homology (Weissmann and Weber, Prog. Nucl. Acid. Res. Mol. Biol., 33: 251, 1986; Roberts et al., J. Interferon Cytokine Res. 18: 805-816, 1998). The human IFNα subtypes are at least IFNαA (IFNα2), IFNαB2 (IFNα8), IFNαC (IFNα10), IFNαD (IFNα1), IFNαF (IFNα21), IFNαG (IFNα5), and IFNαH (IFNα14), IFNαI with P34H substitution (IFNα17), IFNαJ1 (IFNα7), IFNαK (IFNα6), IFNα4b (IFNα4), and IFNαWA (IFNα6). Nomenclature for human interferons is found at: http://www_genenames_org/genefamilies/_IFN. The polypeptide sequences for human interferon-alpha are deposited in database under accession numbers: AAA 52716, AAA 52724, and AAA 52713. The polypeptide sequences for human interferon-beta are deposited in database under accession numbers AAC41702, NP 002167, AAH 96152, AAH 96153, AAH 96150, AAH 96151, AAH 69314, and AAH 36040. The polypeptide sequences for human interferon-gamma are deposited in database under accession numbers AAB 59534, AAM 28885, CAA 44325, AAK 95388, CAA 00226, AAP 20100, AAP 20098, AAK 53058, and NP-000610.

As used herein, the term "inhibitor of type 1 interferons" refers to any compound that is able to inhibit the activity or expression of type 1 interferons. For example, the inhibitor can block the type 1 interferon or block the signalling pathway. In particular, the inhibitor inhibits the binding of type 1 interferons to their receptor. Typically, the inhibitor include polypeptides, antibodies, and inhibitors of expression.

In some embodiments, the inhibitor is a neutralizing antibody. The term "neutralizing antibody" as used herein refers to an antibody or antibody fragment that partially or completely inhibits, by any mechanism, the biological activity mediated by type 1 interferons. Neutralizing antibodies can be identified using any assays for biological activity well known in the art. The neutralizing antibody may inhibit measured the biological activity by 20%, 0.30%, 40%, 50%, 60%, 70%, 75%, 80%, 85%, 90%, 95%, 96%, 97%, 98%, 99% or 100%.

As used herein, the term "antibody" is thus used to refer to any antibody-like molecule that has an antigen binding region, and this term includes antibody fragments that comprise an antigen binding domain such as Fab', Fab, F(ab')2, single domain antibodies (DABs), TandAbs dimer, Fv, scFv (single chain Fv), dsFv, ds-scFv, Fd, linear antibodies, minibodies, diabodies, bispecific antibody fragments, bibody, tribody (scFv-Fab fusions, bispecific or trispecific, respectively); sc-diabody; kappa(lamda) bodies (scFv-CL fusions); BiTE (Bispecific T-cell Engager, scFv-scFv tandems to attract T cells); DVD-Ig (dual variable domain antibody, bispecific format); SIP (small immunoprotein, a kind of minibody); SMIP ("small modular immunopharmaceutical" scFv-Fc dimer; DART (ds-stabilized diabody "Dual Affinity ReTargeting"); small antibody mimetics comprising one or more CDRs and the like. The techniques for preparing and using various antibody-based constructs and fragments are well known in the art (see Kabat et al., 1991, specifically incorporated herein by reference). Diabodies, in particular, are further described in EP 404, 097 and WO 93/1 1 161; whereas linear antibodies are further described in Zapata et al. (1995). Antibodies can be fragmented using conventional techniques. For example, F(ab')2 fragments can be generated by treating the antibody with pepsin. The resulting F(ab')2 fragment can be treated to reduce disulfide bridges to produce Fab' fragments. Papain digestion can lead to the formation of Fab fragments. Fab, Fab' and F(ab')2, scFv, Fv, dsFv, Fd, dAbs, TandAbs, ds-scFv, dimers, minibodies, diabodies, bispecific antibody fragments and other fragments can also be synthesized by recombinant techniques or can be chemically synthesized. Techniques for producing antibody fragments are well known and described in the art. For example, each of Beckman et al., 2006; Holliger & Hudson, 2005; Le Gall et al., 2004; Reff & Heard, 2001; Reiter et al., 1996; and Young et al., 1995 further describe and enable the production of effective antibody fragments. In some embodiments, the antibody of the present invention is a single chain antibody. As used herein the term "single domain antibody" has its general meaning in the art and refers to the single heavy chain variable domain of antibodies of the type that can be found in Camelid mammals which are naturally devoid of light chains. Such single domain antibody are also "nanobody®". For a general description of (single) domain antibodies, reference is also made to the prior art cited above, as well as to EP 0 368 684, Ward et al. (Nature 1989 Oct. 12; 341 (6242): 544-6), Holt et al., Trends Biotechnol., 2003; 21(11):484-490; and WO 06/030220, WO 06/003388.

In some embodiments, the antibody is a humanized antibody. As used herein, "humanized" describes antibodies wherein some, most or all of the amino acids outside the CDR regions are replaced with corresponding amino acids derived from human immunoglobulin molecules. Methods of humanization include, but are not limited to, those described in U.S. Pat. Nos. 4,816,567, 5,225,539, 5,585,089, 5,693,761, 5,693,762 and 5,859,205, which are hereby incorporated by reference.

In some embodiments, the antibody is a fully human antibody. Fully human monoclonal antibodies also can be prepared by immunizing mice transgenic for large portions of human immunoglobulin heavy and light chain loci. See, e.g., U.S. Pat. Nos. 5,591,669, 5,598,369, 5,545,806, 5,545,807, 6,150,584, and references cited therein, the contents of which are incorporated herein by reference.

In some embodiments, the antibody of the present invention is a single chain antibody. As used herein the term "single domain antibody" has its general meaning in the art and refers to the single heavy chain variable domain of antibodies of the type that can be found in Camelid mammals which are naturally devoid of light chains. Such single domain antibody are also "nanobody®".

In some embodiments, the antibody comprises human heavy chain constant regions sequences but will not induce antibody dependent cellular cytotoxicity (ADCC). In some embodiments, the antibody of the present invention does not comprise an Fc domain capable of substantially binding to a FcgRIIIA (CD16) polypeptide. In some embodiments, the antibody of the present invention lacks an Fc domain (e.g. lacks a CH2 and/or CH3 domain) or comprises an Fc domain of IgG2 or IgG4 isotype. In some embodiments, the antibody of the present invention consists of or comprises a Fab, Fab', Fab'-SH, F (ab')2, Fv, a diabody, single-chain antibody fragment, or a multispecific antibody comprising multiple different antibody fragments. In some embodiments, the antibody of the present invention is not linked to a toxic moiety. In some embodiments, one or more amino acids selected from amino acid residues can be replaced with a different amino acid residue such that the antibody has altered C2q binding and/or reduced or abolished complement dependent cytotoxicity (CDC). This approach is described in further detail in U.S. Pat. No. 6,194,551 by Idusogie et al.

In some embodiments, the inhibitor is an inhibitor of expression. An "inhibitor of expression" refers to a natural or synthetic compound that has a biological effect to inhibit the expression of a gene. In a preferred embodiment of the invention, said inhibitor of gene expression is a siRNA, an antisense oligonucleotide or a ribozyme. For example, antisense oligonucleotides, including anti-sense RNA molecules and anti-sense DNA molecules, would act to directly block the translation of type 1 interferon mRNA by binding thereto and thus preventing protein translation or increasing mRNA degradation, thus decreasing the level of type 1 interferon, and thus activity, in a cell. For example, antisense oligonucleotides of at least about 15 bases and complementary to unique regions of the mRNA transcript sequence encoding type 1 interferon can be synthesized, e.g., by conventional phosphodiester techniques. Methods for using antisense techniques for specifically inhibiting gene expression of genes whose sequence is known are well known in the art (e.g. see U.S. Pat. Nos. 6,566,135; 6,566,131; 6,365,354; 6,410,323; 6,107,091; 6,046,321; and 5,981,732). Small inhibitory RNAs (siRNAs) can also function as inhibitors of expression for use in the present invention. Type 1 interferon gene expression can be reduced by contacting a patient or cell with a small double stranded RNA (dsRNA), or a vector or construct causing the production of a small double stranded RNA, such that type 1 interferon gene expression is specifically inhibited (i.e. RNA interference or RNAi). Antisense oligonucleotides, siRNAs, shRNAs and ribozymes of the invention may be delivered in vivo alone or in association with a vector. In its broadest sense, a "vector" is any vehicle capable of facilitating the transfer of the antisense oligonucleotide, siRNA, shRNA or ribozyme nucleic acid to the cells and typically cells expressing type 1 interferon. Typically, the vector transports the nucleic acid to cells with reduced degradation relative to the extent of degradation that would result in the absence of the vector. In general, the vectors useful in the invention include, but are not limited to, plasmids, phagemids, viruses, other vehicles derived from viral or bacterial sources that have been manipulated by the insertion or incorporation of the antisense oligonucleotide, siRNA, shRNA or ribozyme nucleic acid sequences. Viral vectors are a preferred type of vector and include, but are not limited to nucleic acid sequences from the following viruses: retrovirus, such as moloney murine leukemia virus, harvey murine sarcoma virus, murine mammary tumor virus, and rous sarcoma virus; adenovirus, adeno-associated virus; SV40-type viruses; polyoma viruses; Epstein-Barr viruses; papilloma viruses; herpes virus; vaccinia virus; polio virus; and RNA virus such as a retrovirus. One can readily employ other vectors not named but known to the art. In some embodiments, the inhibitor of expression is an endonuclease. The term "endonuclease" refers to enzymes that cleave the phosphodiester bond within a polynucleotide chain. Some, such as Deoxyribonuclease I, cut DNA relatively nonspecifically (without regard to sequence), while many, typically called restriction endonucleases or restriction enzymes, and cleave only at very specific nucleotide sequences. The mechanism behind endonuclease-based genome inactivating generally requires a first step of DNA single or double strand break, which can then trigger two distinct cellular mechanisms for DNA repair, which can be exploited for DNA inactivating: the errorprone nonhomologous end-joining (NHEJ) and the high-fidelity homology-directed repair (HDR). In a particular embodiment, the endonuclease is CRISPR-cas. As used herein, the term "CRISPR-cas" has its general meaning in the art and refers to clustered regularly interspaced short palindromic repeats associated which are the segments of prokaryotic DNA containing short repetitions of base sequences. In some embodiment, the endonuclease is CRISPR-cas9 which is from *Streptococcus pyogenes*. The CRISPR/Cas9 system has been described in U.S. Pat. No. 8,697,359 B1 and US 2014/0068797. In some embodiment, the endonuclease is CRISPR-Cpfl which is the more recently characterized CRISPR from Provotella and *Francisella* 1 (Cpfl) in Zetsche et al. "Cpfl is a Single RNA-guided Endonuclease of a Class 2 CRISPR-Cas System (2015); Cell; 163, 1-13).

A further object of the present invention relates to a method of promoting monocytopoiesis in patient in need thereof comprising administering to the patient a therapeutically effective amount of a type 1 interferon.

In particular, the method is particularly suitable for treating monocytopenia in patient in need thereof. As used herein, the term "monocytopenia" refers to a hematological disorder characterized by an abnormally low number of monocytes.

In some embodiments, the patient has undergone a cytoablative therapy which has caused monocytopenia. The term "cytoablative therapy" has its general meaning in the art and refers to therapy that induce cytoablative effects on rapidly-proliferating cells via several different mechanisms, ultimately leading to cell cycle arrest and/or cellular apoptosis. Typically, the patient has undergone cytoablative therapy before bone marrow transplantation. As used herein, the term "bone marrow transplantation" or "stem cell transplantation" used herein should be considered as interchangeable, referring to the transplantation of stem cells in some form to a recipient. The stem cells do not necessarily have to be derived from bone marrow, but could also be derived from other sources such as umbilical cord blood. As used herein, the terms "hematopoietic stem cell transplantation" or "HSCT" refer to a component of the treatment of a wide array of hematologic disorders. Generally, there are two types of HSCTs: autologous and allogeneic transplantation. As used herein, the term "allogeneic" refers to deriving from, originating in, or being members of the same species, where the members are genetically related or genetically unrelated but genetically similar. An "allogeneic transplant" refers to transfer of cells or organs from a donor to a recipient, where the recipient is the same species as the donor. Allogeneic transplantation involves infusion of donor stem cells, typically using a donor that matches the recipient's MHC. As used herein, the term "autologous" refers to deriving from or originating in the same subject or patient. An "autologous transplant" refers to collection and retransplant of a subject's own cells or organs. Typically cytoablative therapy includes chemotherapy and radiotherapy.

As used herein, the term "radiotherapy" has its general meaning in the art and refers to the medical use of ionizing radiation, generally as part of cancer treatment to control or kill malignant cells.

As used herein the term "chemotherapy" has its general meaning in the art and refers to the medical use of chemotherapeutic agents effective in inhibiting tumor growth. Examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimus tine, trofosfamide, uracil mustard; nitrosureas such as carmustine, chlorozotocin, fotemustine, lomustine, nimustine, ranimustine; antibiotics such as the enediyne antibiotics (e.g. calicheamicin, especially calicheamicin (11 and calicheamicin 211, see, e.g., Agnew Chem Intl. Ed. Engl. 33: 183-186 (1994); dynemicin, including dynemicin A; an esperamicin; as well as neocarzino statin chromophore and related chromoprotein enediyne antibiotic chromomophores), aclacinomysins, actinomycin, authramycin, azaserine, bleomycins, cactinomycin, carabicin, canninomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idanrbicin, marcellomycin, mitomycins, mycophenolic acid, nogalamycin, olivomycins, peplomycin, potfiromycin, puromycin, quelamycin, rodorubicin, streptomgrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidamine; maytansinoids such as maytansine and ansamitocins; mitoguazone; mitoxantrone; mopidamol; nitracrine; pento statin; phenamet; pirarubicin; podophyllinic acid; 2-ethylhydrazide; procarbazine; PSK®; razoxane; rhizoxin; sizofiran; spirogennanium; tenuazonic acid; triaziquone; 2,2',2"-trichlorotriethylarnine; trichothecenes (especially T-2 toxin, verracurin A, roridinA and anguidine); urethan; vindesine; dacarbazine; mannomustine; mitobromtol; mitolactol; pipobroman; gacytosine; arabinoside ("Ara-C"); cyclophosphamide; thiotepa; taxoids, e.g. paclitaxel (TAXOL®, Bristol-Myers Squibb Oncology, Princeton, N.J.) and doxetaxel (TAXOTERE®, Rhone-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-1 1; topoisomerase inhibitor RFS 2000; difluoromethylornithine (DMFO); retinoic acid; capecitabine; and pharmaceutically acceptable salts, acids or derivatives of any of the above. Also included in this definition are antihormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

The method of the present invention is particularly suitable for preventing the immunosuppressive state resulting from monocytopenia (i.e. linked to cytoablative conditioning as above described). In particular, the method of the present invention is suitable for the prophylactic treatment of infectious diseases in patients suffering from monocytopenia. The method of the present invention is also suitable for preventing the immunosuppressive state associated with sepsis, and thus for the prophylactic treatment of infectious diseases that result from said immunosuppressive state.

As used herein the term "infectious disease" includes any infection caused by viruses, bacteria, protozoa, molds or fungi. In some embodiments, the infectious disease is an opportunistic infection. As used herein, the term "opportunistic infection" refers to bacterial, viral, fungal or protozoan infection caused by opportunistic pathogens that may or may not cause diseases in healthy hosts having a functioning immune system. These pathogens may cause an opportunistic infection since a compromised immune system presents an "opportunity" for such pathogens to thrive in an immunocompromised subject. Non-limiting examples of viral infections include Herpes simplex virus (HSV) infections, Cytomegalovirus (CMV) infections, *Varicella-zoster* virus (VZV) infections, Human herpes virus 6 (HHV6) infections, Epstein-Barr virus (EBV) infections, respiratory virus infections (such as respiratory syncytial virus (RSV), parainfluenza virus, rhinovirus, and influenza virus) and adenovirus infections. Non-limiting examples of bacterial infections include Gram-negative bacteria infections such as *Escherichia* (e.g. *Escherichia coli*), *Salmonella, Shigella*, and other Enterobacteriaceae, *Pseudomonas* (e.g. *Pseudomonas aeruginosa*), *Moraxella, Helicobacter,* and *Legionella* infections. Non-limiting examples of fungal infections include *Aspergillus* infection (e.g. *Aspergillus fumigatus*), *Candida* infection (e.g. *Candida albicans* and non-*albicans Candida*) and other emerging fungi infections including *Trichosporon, Alternaria, Fusarium*, and Mucorales infections.

In some embodiments, the type 1 interferon is an interferon-alpha (IFN-a) polypeptide. The term "IFN-a" encompasses derivatives of IFN-a that are derivatized (e.g., are chemically modified relative to the naturally occurring peptide) to alter certain properties such as serum half-life. As such, the term "IFN-a" includes IFN-a derivatized with polyethylene glycol ("PEGylated IFN-a"), and the like. PEGylated IFN-a, and methods for making same, is discussed in, e.g., U.S. Pat. Nos. 5,382,657; 5,951,974; and 5,981,709. PEGylated IFN-a encompasses conjugates of PEG and any of the above-described IFN-a molecules, including, but not limited to, PEG conjugated to interferon alpha-2a (Roferon, Hoffman La-Roche, Nutley, N.J.), interferon alpha-2b (Intron, Schering-Plough, Madison, N.J.), interferon alpha-2c (Berofor Alpha, Boehringer Ingelheim, Ingelheim, Germany); and consensus interferon as defined by determination of a consensus sequence of naturally occurring interferon alphas (Infergen®, InterMune, Inc., Brisbane, Calif.). Thus, in some embodiments, the IFN-a has been modified with one or more polyethylene glycol moieties, i.e., pegylated. Two forms of pegylated-interferon, peginterferon alfa-2a (40 kD) (Pegasys, Hoffmann-La Roche) and peginterferon alfa-2b (12 kD) (PegIntron, Merck), are commercially available, which differ in terms of their pharmacokinetic, viral kinetic, tolerability profiles, and hence, dosing. In particular, Peginterferon alfa-2a (Pegasys) consists of interferon alfa-2a (~20 kD) covalently linked to a 40 kD branched polyethylene glycol (PEG). The PEG moiety is linked at a single site to the interferon alfa moiety via a stable amide bond to lysine. Peginterferon alfa-2a has an approximate molecular weight of 60,000 daltons. The biologic activity of peginterferon-alfa-2a derives from its interferon alfa-2a moiety which impacts both adaptive and innate immune responses against certain viruses. Compared with the native interferon alfa-2a, the peginterferon alfa-2a has sustained absorption, delayed clear. Peginterferon alfa-2a is used as a fixed weekly dose. Peginterferon alfa-2a has a relatively constant absorption after injection and is distributed mostly in the blood and organs.

As used herein, the term "treatment" or "treat" refer to both prophylactic or preventive treatment as well as curative or disease modifying treatment, including treatment of patient at risk of contracting the disease or suspected to have contracted the disease as well as patients who are ill or have been diagnosed as suffering from a disease or medical condition, and includes suppression of clinical relapse. The treatment may be administered to a patient having a medical disorder or who ultimately may acquire the disorder, in order to prevent, cure, delay the onset of, reduce the severity of, or ameliorate one or more symptoms of a disorder or recurring disorder, or in order to prolong the survival of a patient beyond that expected in the absence of such treatment. By "therapeutic regimen" is meant the pattern of treatment of an illness, e.g., the pattern of dosing used during therapy. A therapeutic regimen may include an induction regimen and a maintenance regimen. The phrase "induction regimen" or "induction period" refers to a therapeutic regimen (or the portion of a therapeutic regimen) that is used for the initial treatment of a disease. The general goal of an induction regimen is to provide a high level of drug to a patient during the initial period of a treatment regimen. An induction regimen may employ (in part or in whole) a "loading regimen", which may include administering a greater dose of the drug than a physician would employ during a maintenance regimen, administering a drug more frequently than a physician would administer the drug during a maintenance regimen, or both. The phrase "maintenance regimen" or "maintenance period" refers to a therapeutic regimen (or the portion of a therapeutic regimen) that is used for the maintenance of a patient during treatment of an illness, e.g., to keep the patient in remission for long periods of time (months or years). A maintenance regimen may employ continuous therapy (e.g., administering a drug at a regular intervals, e.g., weekly, monthly, yearly, etc.) or intermittent therapy (e.g., interrupted treatment, intermittent treatment, treatment at relapse, or treatment upon achievement of a particular predetermined criteria [e.g., pain, disease manifestation, etc.]).

As used herein, the term "prophylactic treatment" refers to any medical or public health procedure whose purpose is to prevent a disease. As used herein, the terms "prevent", "prevention" and "preventing" refer to the reduction in the risk of acquiring or developing a given condition, or the reduction or inhibition of the recurrence or said condition in a subject who is not ill, but who has been or may be near a subject with the disease. It is also to be appreciated that the various modes of treatment or prevention of medical conditions as described are intended to mean "substantial,"

which includes total but also less than total treatment or prevention, and wherein some biologically or medically relevant result is achieved.

As used herein, the term "therapeutically effective amount" refers to an amount effective of the active ingredient, at dosages and for periods of time necessary, to achieve a desired therapeutic result. A therapeutically effective amount of the active agent may vary according to factors such as the disease state, age, sex, and weight of the individual, and the ability of the active agent to elicit a desired response in the individual. A therapeutically effective amount is also one in which any toxic or detrimental effects of the antibody or antibody portion are outweighed by the therapeutically beneficial effects. The efficient dosages and dosage regimens for the active agent depend on the disease or condition to be treated and may be determined by the persons skilled in the art. A physician having ordinary skill in the art may readily determine and prescribe the effective amount of the pharmaceutical composition required. For example, the physician could start doses of active agent employed in the pharmaceutical composition at levels lower than that required achieving the desired therapeutic effect and gradually increasing the dosage until the desired effect is achieved. In general, a suitable dose of a composition of the present invention will be that amount of the compound, which is the lowest dose effective to produce a therapeutic effect according to a particular dosage regimen. Such an effective dose will generally depend upon the factors described above.

Typically, the active agent is administered to the patient in the form of a pharmaceutical composition which comprises a pharmaceutically acceptable carrier. Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. For use in administration to a patient, the composition will be formulated for administration to the patient. The compositions of the present invention may be administered orally, parenterally, by inhalation spray, topically, rectally, nasally, buccally, vaginally or via an implanted reservoir. The used herein includes subcutaneous, intravenous, intramuscular, intra-articular, intra-synovial, intrasternal, intrathecal, intrahepatic, intralesional and intracranial injection or infusion techniques. Sterile injectable forms of the compositions of this invention may be aqueous or an oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation. The compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include, e.g., lactose. When aqueous suspensions are required for oral use, the active ingredient is combined with emulsifying and suspending agents. If desired, certain sweetening, flavoring or coloring agents may also be added. Alternatively, the compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols. The compositions of this invention may also be administered topically, especially when the target of treatment includes areas or organs readily accessible by topical application, including diseases of the eye, the skin, or the lower intestinal tract. Suitable topical formulations are readily prepared for each of these areas or organs. For topical applications, the compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water. Topical application for the lower intestinal tract can be effected in a rectal suppository formulation (see above) or in a suitable enema formulation. Patches may also be used. The compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The invention will be further illustrated by the following FIGURES and examples. However, these examples and FIGURES should not be interpreted in any way as limiting the scope of the present invention.

EXAMPLE

Material & Methods

The Murine Model, and Induction of LPS-Induced Endotoxemia.

C57BL/6J mice (from Janvier Labs), Caspase-1-/-65 and Ifnar-/- (kindly provided by U. Muller66) mice at 8 to 16 weeks of age received a retro-orbital, intravenous (IV) injection of 25 µg of LPS (O111:B4 Ultrapure, Invivogen) in 100 µl of Dulbecco's PBS. Control mice received Dulbecco's PBS only. Spleen, blood and BM (femur and tibia) samples were collected at the indicated time points. The local investigational review board approved all animal studies. Animal experiments were performed in an accredited establishment (N° B59-108) according to governmental guidelines N° 86/609/CEE.

Cell Preparation and Flow Cytometry.

BM cells were flushed out of the bones. A single-cell suspension was prepared by repeated pipetting. Spleen samples were disaggregated by 30 minutes of 1 mg/ml Collagenase D (Roche) treatment and a single-cell suspension was prepared by repeated pipetting. Red blood cells were lysed by treatment with 160 mM $NH_4Cl$ and 170 mM Tris. Single-cell suspensions were incubated in the dark with LIVE/DEAD reagent (Thermo Fisher Scientific) for 30 minutes on ice. The cells were then incubated for 10 minutes with purified rat anti-mouse CD16/CD32 (Biolegend, 93 clone) and normal mouse serum (Interchim) before being stained with various monoclonal antibodies for 20 minutes in the dark on ice. Blood sampled in heparinized tubes by cardiac puncture immediately after sacrifice. Whole blood cells were then directly incubated with the antibodies for 20 minutes at room temperature in the dark. Red blood cells were lysed after staining with Optilyse B erythrolytic reagent (Beckman Coulter). Samples were analyzed with a LSR Fortessa flow cytometer (BD Biosciences) or sorted on a BD FACS Aria (BD Biosciences). The data were analyzed with Flowjo software V10.1 (TreeStar). The following antibodies were used for staining (Biolegend): PerCP anti-mouse CD3 (17A2), CD19 (6D5), NK1.1 (PK136), Ly6G (1A8) and Ter119 (TER-119), APC-Cy7 anti-mouse CD11b (M1.70), APC anti-mouse CD115 (AFS98) and CD64 (X54-5/7.1), PE anti-mouse CD135 (A2F10) and CD64 (X54-5/7.1), BV605 anti-mouse Sca1 (D7), Alexa Fluor 700 anti-mouse Ly6C (HK1.4), PeCy7 anti-mouse CD117 (2B8) and CD24 (M1/69), BV711 anti-mouse CD64 (X54-5/7.1), BV510 or FITC anti-mouse I-A/I-E (M5/114.15.2), and FITC anti-mouse CD172a (P84), and anti-mouse BrdU (3D4). The PE-CF594 anti-mouse CD11c (HL3) antibody was purchased from BD Biosciences.

BrdU Incorporation and Intracellular Staining.

Single-cell suspensions of BM cells were incubated for 1 hour in vitro with 10 µM BrdU in complete medium[67]. The cells were then harvested, washed and stained for extracellular markers as described previously. Intracellular BrdU staining was performed using a BrdU Flow Kit (BD Pharmingen), according to the manufacturer's instructions.

In Vitro Culture of BM-Derived DCs.

BM cells were cultured with recombinant human Flt3-L (Celldex) as previously described[5] and supplemented with 100 ng/ml LPS 0111:B4 Ultrapur (Invivogen), 100 ng/ml IFNα (Peprotech), 10 ng/ml IFNβ (Peprotech), or medium only. Cells were harvested, stained and analyzed by flow cytometry on day 7.

Results

LPS-Induced Endotoxemia is Associated to the Development of Mo-APCs in a Type-I IFN Dependent Manner.

To investigate the impact of LPS on the development of Mo-APCs in mice, we counted these APCs in the spleen at various time points after an intravenous (IV) injection of LPS. Single-cell suspensions were prepared from the spleens and analyzed using multiparameter flow cytometry. Live singlet cells were gated on MHCII, and lineage-positive cells (such as T, B and NK cells, eosinophils and neutrophils) were excluded based on CD3, CD19, NK1.1, CCR3, and Ly6G, respectively[6]. Subsequently, Lin$^-$ MHCII$^+$ cells were divided into cDCs and Mo-APCs, based on the latter's expression of CD64 and non-expression of the cDC marker CD135[3,6]. The Mo-APC count had increased significantly 24 h after an IV injection of LPS. Given that hematopoietic progenitor cells can respond to inflammatory cytokines like IFNα and IL-1[39,40], Ifnar and Caspase-1 knock-out mice were injected with LPS or PBS only, and their spleen harvested at 24 h. In contrast to Caspase-1-KO mice, LPS-induced Mo-APCs were not observed in Ifnar-deficient mice and also in the BM of these mice. We found that Caspase-1 was dispensable for the increased proportion of Mo-APC in the BM and spleen following LPS injection. These data indicate that the type-I-IFN-dependent increase in Mo-APC counts is inflammasome-independent. We further analyzed the phenotype of the Mo-APC cells induced 24 h after LPS injection. The CD64$^+$ CD11b$^+$ induced cells have a phenotype reminiscent of the so-called monocyte-waterfall. Briefly, recruited monocytes during inflammation acquire MHCII, and CD64 expression, and lose progressively the marker Ly6C[6]. We observed a significant increase in the population CD64$^+$ CD11b$^+$ Ly6C$^+$ after LPS treatment regardless of MHCII expression in WT and Caspase-1-KO mice, and also in the BM of these mice. These results argue for a monocytic origin of the CD64$^+$ cells induced after LPS treatment. Altogether, these results indicate that LPS-induced endotoxemia is associated to the induction Mo-APC in a type-I IFN manner, independently of inflammasome activation.

LPS-Induced Endotoxemia Impaired Conventional DCs Development.

Spleen DCs (Lin$^-$ CD64$^-$ CD135$^+$ MHCII$^+$ CD11c$^+$) were divided in cDC1 and cDC2 based on the CD11b expression on the latter. Both DC populations were significantly reduced 24 h after LPS treatment in WT mice (relative to control mice injected with PBS only). The lower number of DC in the spleen of untreated Ifnar-KO mice impeded any conclusion on the LPS effect on the development of these cells. The lower DC number in Ifnar-KO is not due to the gating strategy as we take into account the putative lower MHCII level reported in these mice due to the role of type I IFN on DC maturation[41,42] by taking not only the MHCII high cells but also the intermediate ones. We concluded that the increase in the Mo-APC count was accompanied by a decrease in the DC number. In order to study this mechanism in more details, we counted the numbers of direct DC precursors (namely pre-DCs) in the BM 24 h after the LPS injection. The pre-DC was gated as Lin$^-$ CD115$^+$ CD11c$^+$ MHCII$^-$ CD135$^+$ live singlet cells[25]. In WT animals, the absolute count of pre-DCs in the BM was significantly reduced 24 h after LPS injection; this observation is consistent with a decreased number of DCs during LPS-mediated inflammation. To establish whether this affected pre-DC count following LPS treatment were dependent on type I IFNs, we counted the BM pre-DCs in Ifnar-KO mice after LPS injection. We found that LPS-induced BM pre-DCs reduction is type I IFN independent.

These results argue for a reduction of conventional dendritic cells and their pre-DC precursor during LPS-induced endotoxemia.

LPS-Induced Endotoxemia Stimulated Monocytopoiesis.

To determine whether the LPS-mediated induction of Mo-APC is correlated with an induction of monocytopoiesis, we counted the recently described monocyte committed progenitors (namely cMoP) 24 h after LPS injection. The cMoP was gated as described previously[10,25,43]. Briefly, live singlet Lin$^-$ CD115$^+$ CD11c$^-$ MHCII$^-$ Ly6C$^+$ cells were analyzed for Ly6C vs. CD11b, CD117 vs. CD11b, or Sca-1 vs. CD11b, in order to distinguish between cMoPs (live singlet Lin$^-$ CD115$^+$ CD11c$^-$ MHCII$^-$ Ly6C$^+$ CD117$^+$ CD11b$^-$ cells), and monocytes (live singlet Lin$^-$ CD115$^+$ CD11c$^-$ MHCII$^-$ Ly6C$^+$ Sca-1$^-$ CD11b$^+$ cells). At 24 h after LPS injection, monocytes were significantly decreased in the BM and in the blood of WT and Ifnar-KO mice. This drop of BM monocytes might reflect a higher recruitment of these cells towards the peripheral organs, such as the spleen, to favor the generation of LPS-induced Mo-APC. To determine the effects of LPS on cMoPs, BM cells were counted in WT mice after an injection of LPS or PBS. As reported previously in the context of bacterial infection[44], a significant drop in the number of cMoP precursor cells was observed 24 h after LPS injection. These observations indicate that LPS rapidly induces a loss of cMoPs. To determine whether this decrease in cMoPs resulted from accelerated differentiation into monoblasts and promonocyte (pro-Mo) cells (as suggested by[44]), we counted these precursors in the BM. Monoblasts were defined as live singlet Lin$^-$ CD115$^+$ CD11c$^-$ MHCII$^-$ Ly6C$^+$ Sca-1$^+$ CD11b$^-$ cells, and pro-Mo cells were defined as live singlet Lin$^-$ CD115$^+$ CD11c$^-$ MHCII$^-$ Ly6C$^+$ Sca-1$^+$ CD11b$^+$ cells[44]. We detected a significant increase in the BM number of monoblasts and pro-Mo cells after LPS injection (relative to PBS injection). This observation indicates that LPS treatment induces monocytopoiesis in the BM. Given that cMoP cells express the Ifnar[10], we next determined the impact of LPS injection on monocytopoiesis in Ifnar-KO mice. As had been observed in WT animals, we found that the cMoP count in the BM of Ifnar-KO mice had decreased 24 h after LPS injection. Although LPS-induced fall in the cMoP count was Ifnar-independent, LPS-induced increase in monoblast and pro-Mo counts was Ifnar-dependent. As positive and negative effects of type-I IFN on hematopoietic precursor cells are described in the literature[17], we measured the proliferation and number of LSK BM cells (Lin$^-$ Sca-1$^+$ c-kit$^+$)[44,45]. LSK cells were gated[44], and a significant increase of their number and proliferation, evaluated by BrdU incorporation, was observed in a type-I IFN independent manner. Then, LPS induced the generation of monocyte precursors 24 h after its injection in a type-I dependent manner. These observations indicates that the LPS-dependent increase in the BM monoblast and pro-Mo counts was type I IFN signaling dependent. This finding indicates that LPS-induced monocytopoiesis requires intact Ifnar signaling.

LPS Induced Mo-APC on Macrophage/Dendritic Cell Precursor in Type-I IFN Manner.

With a view to establish whether LPS induces monocytopoiesis by modulating the development of BM cells, we studied in vitro cultures of Flt3-L-derived DCs[5]. To establish whether LPS can induce Mo-APC by modulating progenitor development in Flt3-L-DCs, we titrated the induction of Mo-APCs (live singlet MHCII$^+$ CD11c$^+$ CD64$^+$ cells) in response to increasing concentrations of LPS in the culture. We found that LPS concentrations ranging from 10 to 1000 ng/ml induced Mo-APCs. To confirm the monocytic origin of these in vitro generated Mo-APCs, we sorted MDP, CDP and cMoP and cultured them on filler cells in the presence of Flt3-L or Flt3-L and LPS to measure the origin of the induced Mo-APC. As expected only MDP and cMoP cells were able to generate Mo-APC in the presence of LPS. These results showed that LPS addition during in vitro cultures of Flt3-L-derived DCs induced Mo-APC. To determine whether type I IFN signaling is required for the generation of LPS-induced Mo-APCs in BM cells, we compared Ifnar-KO and WT BM cells cultured with Flt3-L in the presence of LPS. Flt3-L-DCs were analyzed in order to determine the proportions of Mo-APCs (live singlet MHCII$^+$ CD11c$^+$ CD64$^+$ cells), cDC s (live singlet MHCII$^+$ CD11c$^+$ CD64$^-$ CD24$^+$ CD172a$^-$ cells) and cDC2s (live singlet MHCII$^+$ CD11c$^+$ CD64$^-$ CD24$^-$ CD172a$^+$ cells). As expected, we found very few Mo-APCs in the Flt3-L-DC culture. However, cDC1s and cDC2s were present in both WT and Ifnar-KO BM. In contrast to experiments with Flt3-L alone, the addition of LPS to the Flt3-L-BM culture at day 0 was associated with a significant increase in the number of Mo-APCs. These results indicate that early addition of LPS to Flt3-L-BM culture system makes the latter a good model of LPS-induced monocytopoiesis. To establish whether type I IFN signaling is required for LPS-induced monocytopoiesis, Ifnar-KO BM cells were compared with WT BM cells in a LPS-Flt3-L-BM culture. We observed that Ifnar-KO BM cells produced fewer Mo-APCs, which is consistent with a crucial role of type I IFN in LPS-induced monocytopoiesis.

To establish whether type I IFN is able to influence MDP progenitors and favor their differentiation into Mo-APCs, MDPs from CD45.2$^+$ mice were sorted and cultured on CD45.1$^+$ filler cells[43] in the presence of Flt3-L and in the presence or absence of IFNα, IFNβ or LPS. We gated on the progeny of the precursor cells by selecting live singlet CD45.2$^+$ MHCII$^+$ cells and analyzed frequencies of Mo-APCs, cDC1 s and cDC2s after 7 days of culture. As expected, purified MDP donor cells gave rise to only cDC1s and cDC2s in the presence of Flt3-L. The addition of IFNα or IFNβ at day 0 of the Flt3-L-DC culture induced a significant increase in Mo-APC counts. Addition of LPS favored Mo-APC induction and impaired DC generation; in contrast, addition of IFNα/β was not associated with a decrease in DC differentiation despite Mo-APC generation. These observations indicate that IFNα/β acts on BM cells to drive the generation of MDP-derived Mo-APCs.

Discussion:

Here, we demonstrated that LPS induces monocytopoiesis in a type-I-IFN-dependent manner at the expense of DC development. Furthermore, we showed for the first time that type I IFN, IFNα and IFNβ, modulate the fate of MDP and increase monocytic progeny. Our results indicate that type I IFN signaling in an inflammatory environment favors the generation of immune cells.

Sepsis is generally characterized by a decrease in the DC count[23-28]. The DC count is decreased directly by inducing DC apoptosis[12,18,26,46] and/or decreasing DC generation[44]. For instance, the DC content decreases after a bacterial infection as a result of a decrease in the number of pre-DC precursors, with no change in the level of apoptosis[44]. Here, by using the discriminating marker CD64 and a murine model of endotoxemia, we noted a rapid increase in the Mo-APC count and a decrease of DC numbers in spleens[6]. Indeed, we observed a decrease in splenic cDCs counts after in vivo LPS treatment, which is consistent with the reduction in the pre-DC numbers in bone marrow. Moreover, in vitro addition of LPS induced a similar decrease in cDCs composition of Flt3-L-derived DCs. This LPS-induced reduction in cDCs is counterbalanced by a type I IFN dependent generation of Mo-APC. The exact mechanism by which LPS reduced pre-DC precursors and cDCs requires more future analysis.

Induction of monocytopoiesis has been reported in various sepsis-related models. In mice, the monocytopoiesis induced by bacterial infections (e.g. with *Yersinia enterocolitica*) is similar to that observed upon LPS treatment[44]. In fact, the cMoP count decreases rapidly in a TLR4- and IFNγ-dependent manner, leading to high numbers of Sca-1$^+$ monoblasts and promonocytes[44]. Similarly, LPS induces a decrease in numbers of the upstream MDP precursor, namely the granulocyte-macrophage progenitor[47]. Moreover, monocytopoiesis during *Listeria monocytogenes* infection is characterized by a significant, Caspase-1-independent increase in the number and proliferation of BM monocytes[48].

In LPS-induced monocytopoiesis, the exact source of type I IFN, the IFN's target cells and other synergistic factors remain to be identified. Plasmacytoid DCs are a candidate for the source of type I IFN, since their number increases in a burn injury model (relative to a sham intervention)[49], their depletion diminishes LPS-induced acute lung injury[50], and chronic TLR7 stimulation results in their type I IFN production which promotes the development of neutrophils in the bone marrow[51]. Hematopoietic cells (including HCS and myeloid precursors) can be considered as targets for type I IFN. Indeed, type I IFN acts on hematopoietic cells and is required for survival in a mouse CLP-based sepsis model by increasing CXCL10 production, recruiting neutrophils and macrophages, and stimulating phagocyte functions[38]. Moreover, we found that LPS and IFNα/β were capable of inducing ex vivo Mo-APCs in the BM, which predominantly contains hematopoietic cells. More precisely, we hypothesize that MDPs and cMoPs might be direct targets of type I IFN, as they express the Ifnar2 receptor protein[10]. Another target cell of type I IFN is monocyte, which responds to this trigger by producing IL-18 during viral infection[52]. However, we cannot rule out the possibility that type I IFN modulates progenitor cells indirectly by inducing other factors. With regard to type I IFN synergistic factors, IFNγ induces the differentiation of myeloid precursors and a decrease in the generation of neutrophils (in viral infections)[53] or DCs (in bacterial infections)[44]. Similarly, IFNγ induces IL-27 production during malaria infection; IL-27 then promotes the expansion and differentiation of long term hematopoietic stem cells (HSCs) into myeloid progenitors, in synergy with stem cell factor (a c-kit ligand)[54]. In a mouse model of acute abdominal sepsis, IL-3 produced by B cells promotes a cytokine storm by inducing the differentiation of Ly6C$^{hi}$ monocytes and neutrophils[55]. Blocking IL-3 production reduces the intensity of sepsis by decreasing inflammation-associated myelopoiesis[55]. Interestingly, IFN-I-activated B cells are protective in early innate immune responses during bacterial sepsis[56].

Unexpectedly, we observed a significant decrease of cMoP counts at 24 h after LPS injection in BM; this apparently contradicts the type-I-IFN-dependent increase in the BM content of Sca-1-expressing monoblast, promonocyte precursor cells and LSK cells. Given that IFNα induces Sca-1 expression in HSCs[57], type I IFN signaling might modulate a rapid transition from Sca-1-negative cells to Sca-1 positive cells. However, we saw no impact of Ifnar deficiency on LSK cell number and proliferation. Suggesting that our results cannot be explained by a decreased Sca-1 expression or HSC proliferation in Ifnar deficient mice. Sca-1 is not only a widely used HSC marker but is also required for HSC self-renewal and the development of committed progenitor cells[58]. Along the same lines, Sca-1 has a crucial role during severe bacterial infections in mice by diverting early hematopoietic precursors towards the myeloid lineage[59]. Moreover, HSCs lacking Sca-1 (like those lacking the Ifnar) are insensitive to IFNα stimulation[17]; this observation demonstrates that Sca-1 mediates the IFNα-induced proliferation of HSCs.

We hypothesize that in an inflammatory context (such as that created by exposure to LPS), type I IFN drives emergency monocytopoiesis by increasing the monocytic output of MDPs. Our present results show that exposure to LPS (a surrogate of bacterial septicemia) leads to type-I-IFN dependent monocytopoiesis by favoring the differentiation of MDPs into Mo-APCs. Although type-I-IFN-dependent monocytopoiesis might represent a potential escape mechanism for viruses[60], it may enable the host to contain the invading pathogen by increasing the availability of innate immune cells. Our observations might be applicable to other biological situations in which overproduction of type I IFN production is observed, such as viral infections and interferon-related diseases[61,51]. Furthermore, we suggest that our findings might also apply to other CD11c-expressing cells, such as regulatory DCs (which expand during endotoxic shock[62]) and inflammatory DCs[63]. Our study opens up opportunities for detailed analyses of type-I-IFN-dependent monocytopoiesis in various inflammatory settings. Although monocytopoiesis is detrimental in the early acute sepsis phase (due to an enhanced inflammatory state), it is beneficial in the late immunosuppressive phase[64]. Based on our results in the mouse, we suggest that the cDC/Mo-APC content in septic patients should be re-evaluated. Unfortunately, the CD64 marker is not discriminative for human cDCs, although other gating strategies have been recently proposed[3]. Moreover, our in vitro model of progenitors cultured on filler cells might be a useful tool for determining the progenitors on which type I IFNs acts to favor monocytopoiesis. In fact, the culture system dissociates the contrasting positive and negative effects of type I IFN on HSCs without affecting the modulation of downstream targets like MDPs and cMoPs[7]. The molecular mechanisms by which type I IFNs render the host more vulnerable to secondary bacterial challenge (including exposure to other PAMPs such as bacterial muramyl dipeptide) merit further study. In summary, our findings describe the molecular mechanism of endotoxemia-associated monocytopoiesis and thus open up new perspectives for immunotherapeutic strategies in the fight against systemic microbial infections. For example, treatment with IFNα might restore normal monocytopoiesis and reduce susceptibility to secondary infections and/or the persistence of some viruses. Similarly, administration of anti-IFNα neutralizing antibodies would be suitable for the treatment of monocyte-dependent inflammatory disorders.

REFERENCES

Throughout this application, various references describe the state of the art to which this invention pertains. The disclosures of these references are hereby incorporated by reference into the present disclosure.

1 Nagai, Y. et al. Toll-like receptors on hematopoietic progenitor cells stimulate innate immune system replenishment. Immunity 24, 801-812, doi:10.1016/j.immuni.2006.04.008 (2006).

2 Esplin, B. L. et al. Chronic exposure to a TLR ligand injures hematopoietic stem cells. J Immunol 186, 5367-5375, doi:10.4049/jimmunol.1003438 (2011).
3 Guilliams, M. et al. Unsupervised High-Dimensional Analysis Aligns Dendritic Cells across Tissues and Species. Immunity 45, 669-684, doi:10.1016/j.immuni.2016.08.015 (2016).
4 Guilliams, M. et al. Dendritic cells, monocytes and macrophages: a unified nomenclature based on ontogeny. Nat Rev Immunol 14, 571-578, doi:10.1038/nri3712 (2014).
5 Naik, S. H. et al. Cutting edge: generation of splenic CD8+ and CD8- dendritic cell equivalents in Fms-like tyrosine kinase 3 ligand bone marrow cultures. J Immunol 174, 6592-6597 (2005).
6 Tamoutounour, S. et al. CD64 distinguishes macrophages from dendritic cells in the gut and reveals the Th1-inducing role of mesenteric lymph node macrophages during colitis. Eur J Immunol 42, 3150-3166, doi:10.1002/eji.201242847 (2012).
7 Langlet, C. et al. CD64 expression distinguishes monocyte-derived and conventional dendritic cells and reveals their distinct role during intramuscular immunization. J Immunol 188, 1751-1760, doi:10.4049/jimmunol.1102744 (2012).
8 Gautier, E. L. et al. Gene-expression profiles and transcriptional regulatory pathways that underlie the identity and diversity of mouse tissue macrophages. Nat Immunol 13, 1118-1128, doi:10.1038/ni.2419 (2012).
9 Laoui, D. et al. The tumour microenvironment harbours ontogenically distinct dendritic cell populations with opposing effects on tumour immunity. Nat Commun 7, 13720, doi:10.1038/ncomms13720 (2016).
10 Hettinger, J. et al. Origin of monocytes and macrophages in a committed progenitor. Nat Immunol 14, 821-830, doi:10.1038/ni.2638 (2013).
11 Schraml, B. U. & Reis e Sousa, C. Defining dendritic cells. Curr Opin Immunol 32, 13-20, doi:10.1016/j.coi.2014.11.001 (2015).
12 Hotchkiss, R. S. et al. Depletion of dendritic cells, but not macrophages, in patients with sepsis. J Immunol 168, 2493-2500 (2002).
13 Bohannon, J., Cui, W., Sherwood, E. & Toliver-Kinsky, T. Dendritic cell modification of neutrophil responses to infection after burn injury. J Immunol 185, 2847-2853, doi:10.4049/jimmunol.0903619 (2010).
14 Toliver-Kinsky, T. E., Cui, W., Murphey, E. D., Lin, C. & Sherwood, E. R. Enhancement of dendritic cell production by fms-like tyrosine kinase-3 ligand increases the resistance of mice to a burn wound infection. J Immunol 174, 404-410 (2005).
15 Toliver-Kinsky, T. E., Lin, C. Y., Herndon, D. N. & Sherwood, E. R. Stimulation of hematopoiesis by the Fms-like tyrosine kinase 3 ligand restores bacterial induction of Th1 cytokines in thermally injured mice. Infect Immun 71, 3058-3067 (2003).
16 Benjamim, C. F., Lundy, S. K., Lukacs, N. W., Hogaboam, C. M. & Kunkel, S. L. Reversal of long-term sepsis-induced immunosuppression by dendritic cells. Blood 105, 3588-3595, doi:10.1182/blood-2004-08-3251 (2005).
17 Essers, M. A. et al. IFNalpha activates dormant haematopoietic stem cells in vivo. Nature 458, 904-908, doi:10.1038/nature07815 (2009).
18 Hotchkiss, R. S., Monneret, G. & Payen, D. Sepsis-induced immunosuppression: from cellular dysfunctions to immunotherapy. Nat Rev Immunol 13, 862-874, doi:10.1038/nri3552 (2013).
19 Heumann, D. & Roger, T. Initial responses to endotoxins and Gram-negative bacteria. Clin Chim Acta 323, 59-72 (2002).
20 Cohen, J. et al. Sepsis: a roadmap for future research. Lancet Infect Dis 15, 581-614, doi:10.1016/S1473-3099(15)70112-X (2015).
21 Biswas, S. K. & Lopez-Collazo, E. Endotoxin tolerance: new mechanisms, molecules and clinical significance. Trends Immunol 30, 475-487, doi:10.1016/j.it.2009.07.009 (2009).
22 Hotchkiss, R. S. & Sherwood, E. R. Immunology. Getting sepsis therapy right. Science 347, 1201-1202, doi:10.1126/science.aaa8334 (2015).
23 Gautier, E. L. et al. Enhanced dendritic cell survival attenuates lipopolysaccharide-induced immunosuppression and increases resistance to lethal endotoxic shock. J Immunol 180, 6941-6946 (2008).
24 Efron, P. A. et al. Characterization of the systemic loss of dendritic cells in murine lymph nodes during polymicrobial sepsis. J Immunol 173, 3035-3043 (2004).
25 Autenrieth, S. E. et al. Immune evasion by *Yersinia enterocolitica*: differential targeting of dendritic cell subpopulations in vivo. PLoS Pathog 6, e1001212, doi:10.1371/journal.ppat.1001212 (2010).
26 De Smedt, T. et al. Regulation of dendritic cell numbers and maturation by lipopolysaccharide in vivo. J Exp Med 184, 1413-1424 (1996).
27 Pene, F. et al. Toll-like receptors 2 and 4 contribute to sepsis-induced depletion of spleen dendritic cells. Infect Immun 77, 5651-5658, doi:10.1128/IAI.00238-09 (2009).
28 Sundquist, M. & Wick, M. J. *Salmonella* induces death of CD8alpha(+) dendritic cells but not CD11c(int)CD11b(+) inflammatory cells in vivo via MyD88 and TNFR1. J Leukoc Biol 85, 225-234, doi:10.1189/jlb.0708413 (2009).
29 Pene, F. et al. Dendritic cells modulate lung response to *Pseudomonas aeruginosa* in a murine model of sepsis-induced immune dysfunction. J Immunol 181, 8513-8520 (2008).
30 Scumpia, P. O. et al. CD11c+ dendritic cells are required for survival in murine polymicrobial sepsis. J Immunol 175, 3282-3286 (2005).
31 Laupland, K. B. Incidence of bloodstream infection: a review of population-based studies. Clin Microbiol Infect 19, 492-500, doi:10.1111/1469-0691.12144 (2013).
32 Creagh, E. M. & O'Neill, L. A. TLRs, NLRs and RLRs: a trinity of pathogen sensors that co-operate in innate immunity. Trends Immunol 27, 352-357, doi:10.1016/j.it.2006.06.003 (2006).
33 Hertzog, P. J., O'Neill, L. A. & Hamilton, J. A. The interferon in TLR signaling: more than just antiviral. Trends Immunol 24, 534-539 (2003).
34 Karaghiosoff, M. et al. Central role for type I interferons and Tyk2 in lipopolysaccharide-induced endotoxin shock. Nat Immunol 4, 471-477, doi:10.1038/ni910 (2003).
35 Thomas, K. E., Galligan, C. L., Newman, R. D., Fish, E. N. & Vogel, S. N. Contribution of interferon-beta to the murine macrophage response to the toll-like receptor 4 agonist, lipopolysaccharide. J Biol Chem 281, 31119-31130, doi:10.1074/jbc.M604958200 (2006).
36 de Weerd, N. A., Samarajiwa, S. A. & Hertzog, P. J. Type I interferon receptors: biochemistry and biological functions. J Biol Chem 282, 20053-20057, doi:10.1074/jbc.R700006200 (2007).
37 Platanias, L. C. Mechanisms of type-I- and type-II-interferon-mediated signalling. Nat Rev Immunol 5, 375-386, doi:10.1038/nri1604 (2005).

38 Kelly-Scumpia, K. M. et al. Type I interferon signaling in hematopoietic cells is required for survival in mouse polymicrobial sepsis by regulating CXCL10. J Exp Med 207, 319-326, doi:10.1084/jem.20091959 (2010).

39 Takizawa, H., Boettcher, S. & Manz, M. G. Demand-adapted regulation of early hematopoiesis in infection and inflammation. Blood 119, 2991-3002, doi:10.1182/blood-2011-12-380113 (2012).

40 Ueda, Y., Cain, D. W., Kuraoka, M., Kondo, M. & Kelsoe, G. IL-1R type I-dependent hemopoietic stem cell proliferation is necessary for inflammatory granulopoiesis and reactive neutrophilia. J Immunol 182, 6477-6484, doi:10.4049/jimmunol.0803961 (2009).

41 Le Bon, A. et al. Cross-priming of CD8+ T cells stimulated by virus-induced type I interferon. Nat Immunol 4, 1009-1015, doi:10.1038/ni978 (2003).

42 Hou, L. et al. Type 1 interferon-induced IL-7 maintains CD8+ T-cell responses and homeostasis by suppressing PD-1 expression in viral hepatitis. Cell Mol Immunol 12, 213-221, doi:10.1038/cmi.2014.49 (2015).

43 Helft, J. et al. GM-CSF Mouse Bone Marrow Cultures Comprise a Heterogeneous Population of CD11c(+) MHCII(+) Macrophages and Dendritic Cells. Immunity 42, 1197-1211, doi:10.1016/j.immuni.2015.05.018 (2015).

44 Pasquevich, K. A. et al. Innate immune system favors emergency monopoiesis at the expense of DC-differentiation to control systemic bacterial infection in mice. Eur J Immunol 45, 2821-2833, doi:10.1002/eji.201545530 (2015).

45 Baldridge, M. T., King, K. Y. & Goodell, M. A. Inflammatory signals regulate hematopoietic stem cells. Trends Immunol 32, 57-65, doi:10.1016/j.it.2010.12.003 (2011).

46 Peck-Palmer, O. M. et al. Modulation of the Bcl-2 family blocks sepsis-induced depletion of dendritic cells and macrophages. Shock 31, 359-366, doi:10.1097/SHK.0b013e31818ba2a2 (2009).

47 Rodriguez, S. et al. Dysfunctional expansion of hematopoietic stem cells and block of myeloid differentiation in lethal sepsis. Blood 114, 4064-4076, doi:10.1182/blood-2009-04-214916 (2009).

48 Serbina, N. V., Hohl, T. M., Cherny, M. & Pamer, E. G. Selective expansion of the monocytic lineage directed by bacterial infection. J Immunol 183, 1900-1910, doi: 10.4049/jimmunol.0900612 (2009).

49 Johnson, N. B. et al. Perturbed MafB/GATA1 axis after burn trauma bares the potential mechanism for immune suppression and anemia of critical illness. J Leukoc Biol 100, 725-736, doi:10.1189/jlb.1A0815-377R (2016).

50 Mandl, M. et al. Evaluation of the BDCA2-DTR Transgenic Mouse Model in Chronic and Acute Inflammation. PLoS One 10, e0134176, doi:10.1371/journal.pone.0134176 (2015).

51 Buechler, M. B., Teal, T. H., Elkon, K. B. & Hamerman, J. A. Cutting edge: Type I IFN drives emergency myelopoiesis and peripheral myeloid expansion during chronic TLR7 signaling. J Immunol 190, 886-891, doi: 10.4049/jimmunol.1202739 (2013).

52 Lee, A. J. et al. Inflammatory monocytes require type I interferon receptor signaling to activate NK cells via IL-18 during a mucosal viral infection. J Exp Med 214, 1153-1167, doi:10.1084/jem.20160880 (2017).

53 de Bruin, A. M. et al. IFNgamma induces monopoiesis and inhibits neutrophil development during inflammation. Blood 119, 1543-1554, doi:10.1182/blood-2011-07-367706 (2012).

54 Furusawa, J. et al. Promotion of Expansion and Differentiation of Hematopoietic Stem Cells by Interleukin-27 into Myeloid Progenitors to Control Infection in Emergency Myelopoiesis. PLoS Pathog 12, e1005507, doi: 10.1371/journal.ppat.1005507 (2016).

55 Weber, G. F. et al. Interleukin-3 amplifies acute inflammation and is a potential therapeutic target in sepsis. Science 347, 1260-1265, doi:10.1126/science.aaa4268 (2015).

56 Kelly-Scumpia, K. M. et al. B cells enhance early innate immune responses during bacterial sepsis. J Exp Med 208, 1673-1682, doi:10.1084/jem.20101715 (2011).

57 King, K. Y. & Goodell, M. A. Inflammatory modulation of HSCs: viewing the HSC as a foundation for the immune response. Nat Rev Immunol 11, 685-692, doi: 10.1038/nri3062 (2011).

58 Ito, C. Y., Li, C. Y., Bernstein, A., Dick, J. E. & Stanford, W. L. Hematopoietic stem cell and progenitor defects in Sca-1/Ly-6A-null mice. Blood 101, 517-523, doi: 10.1182/blood-2002-06-1918 (2003).

59 Zhang, P. et al. The lineage-c-Kit+ Sca-1+ cell response to *Escherichia coli* bacteremia in Balb/c mice. Stem Cells 26, 1778-1786, doi:10.1634/stemcells.2007-1027 (2008).

60 McNab, F., Mayer-Barber, K., Sher, A., Wack, A. & O'Garra, A. Type I interferons in infectious disease. Nat Rev Immunol 15, 87-103, doi:10.1038/nri3787 (2015).

61 Sato, T. et al. Interferon regulatory factor-2 protects quiescent hematopoietic stem cells from type I interferon-dependent exhaustion. Nat Med 15, 696-700, doi: 10.1038/nm.1973 (2009).

62 Wong, K. A. & Rodriguez, A. *Plasmodium* infection and endotoxic shock induce the expansion of regulatory dendritic cells. J Immunol 180, 716-726 (2008).

63 Greter, M. et al. GM-CSF controls nonlymphoid tissue dendritic cell homeostasis but is dispensable for the differentiation of inflammatory dendritic cells. Immunity 36, 1031-1046, doi:10.1016/j.immuni.2012.03.027 (2012).

64 Meisel, C. et al. Granulocyte-macrophage colony-stimulating factor to reverse sepsis-associated immunosuppression: a double-blind, randomized, placebo-controlled multicenter trial. Am J Respir Crit Care Med 180, 640-648, doi:10.1164/rccm.200903-03630C (2009).

65 Kuida, K. et al. Altered cytokine export and apoptosis in mice deficient in interleukin-1 beta converting enzyme. Science 267, 2000-2003 (1995).

66 Muller, U. et al. Functional role of type I and type II interferons in antiviral defense. Science 264, 1918-1921 (1994).

67 Sarrazin, S. et al. MafB restricts M-CSF-dependent myeloid commitment divisions of hematopoietic stem cells. Cell 138, 300-313, doi:10.1016/j.cell.2009.04.057 (2009).

The invention claimed is:

1. A method of reducing monocytopoiesis in a patient in need thereof comprising administering to the patient a therapeutically effective amount of an anti-IFNα neutralizing antibody, wherein the patient has a cancer, and the an anti-IFNα neutralizing antibody reduces monocytopoiesis in the patient.

2. The method of claim 1 wherein the patient has an early acute sepsis.

3. The method of claim 1 wherein the inhibitor of type I interferons inhibits tumor infiltration of monocytic myeloid-derived suppressor cells.

4. The method of claim 1 wherein the cancer is selected from the group consisting of neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous; adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; and roblastoma, malignant; Sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor; mullerian mixed tumor; nephroblastoma; hepatoblastoma; carcinosarcoma; mesenchymoma,; brenner tumor; phyllodes tumor; synovial sarcoma; mesothelioma,; dysgerminoma; embryonal carcinoma; teratoma; struma ovarii; choriocarcinoma; mesonephroma; hemangiosarcoma; hemangioendothelioma; kaposi's sarcoma; hemangiopericytoma; lymphangiosarcoma; osteosarcoma; juxtacortical osteosarcoma; chondrosarcoma; chondroblastoma; mesenchymal chondrosarcoma; giant cell tumor of bone; ewing's sarcoma; odontogenic tumor; ameloblastic odontosarcoma; ameloblastoma; ameloblastic fibrosarcoma; pinealoma; chordoma; glioma; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma; neurofibrosarcoma; neurilemmoma; granular cell tumor; malignant lymphoma; Hodgkin's disease; Hodgkin's lymphoma; paragranuloma;, small lymphocytic malignant lymphoma; large cell, diffuse malignant lymphoma; follicular malignant lymphoma; mycosis fungoides; non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

5. The method of claim 1 further comprising administering an immune checkpoint inhibitor to the patient.

6. The method of claim 5 wherein the immune checkpoint inhibitor is an antibody selected from the group consisting of anti-CTLA4 antibodies, anti-PD-1 antibodies, anti-PD-L1 antibodies, anti-PD-L2 antibodies anti-TIM-3 antibodies, anti-LAG3 antibodies, anti-B7H3 antibodies, anti-B7H4 antibodies, anti-BTLA antibodies, and anti-B7H6 antibodies.

7. The method of claim 1, further comprising determining conventional dendritic cell (cDC) and monocyte-derived antigen-presenting cell (Mo-APC) content of the patient.

* * * * *